United States Patent [19]

Uhlarik

[11] Patent Number: 5,115,679
[45] Date of Patent: May 26, 1992

[54] LEVEL MEASURING BUBBLER TUBE TIP

[75] Inventor: William J. Uhlarik, Whittier, Calif.

[73] Assignee: ITT Corporation, New York, N.Y.

[21] Appl. No.: 704,498

[22] Filed: May 23, 1991

Related U.S. Application Data

[63] Continuation of Ser. No. 533,608, Jun. 5, 1990, abandoned.

[51] Int. Cl.⁵ .................. G01F 23/14; G08B 21/00
[52] U.S. Cl. ........................................ 73/302; 73/438
[58] Field of Search ............... 73/290 R, 299, 438, 73/302

[56] References Cited

U.S. PATENT DOCUMENTS

| | | | |
|---|---|---|---|
| 1,399,205 | 12/1921 | Frey | 73/302 |
| 1,720,159 | 7/1929 | Willmann | 73/302 X |
| 3,422,682 | 1/1969 | Evans et al. | 73/438 |
| 3,475,959 | 11/1969 | Glassey | 73/302 X |
| 4,630,478 | 12/1986 | Johnson | 73/299 |
| 5,059,954 | 10/1991 | Beldham et al. | 73/302 X |

Primary Examiner—Daniel M. Yasich
Attorney, Agent, or Firm—Menotti J. Lombardi

[57] ABSTRACT

A level measuring system for measuring the level of a fluid in a tank employing tubes through which gas is passed extending to different levels in the fluid, whereby the level may be measured by comparing the differences in pressure necessary to release bubbles from the tubes. The ends of each of the tubes are bent at substantially a right angle, with the tips cut off at an angle so that the gas/liquid interface of the bubbles are at a more constant depth, and the bubbles are prevented from sagging.

3 Claims, 2 Drawing Sheets

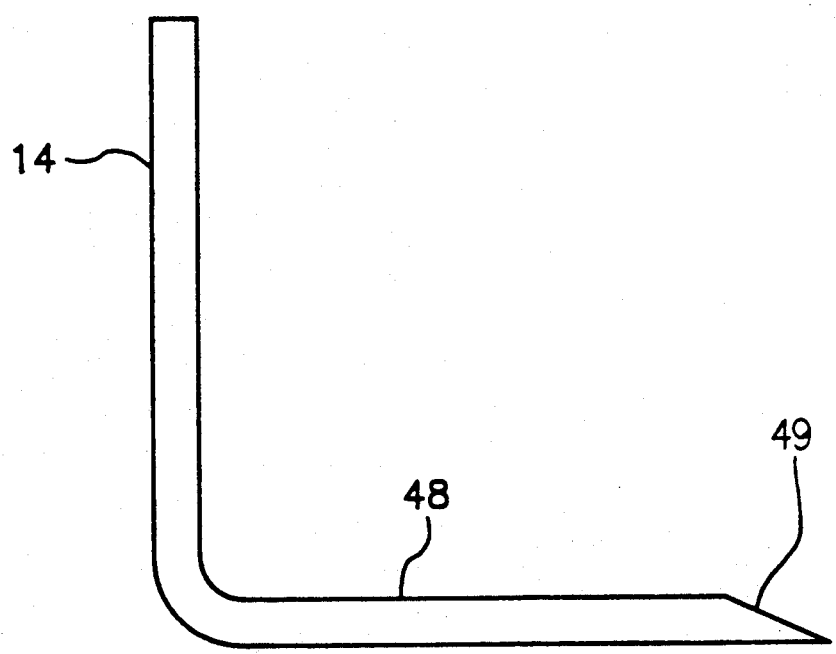
Fig.2
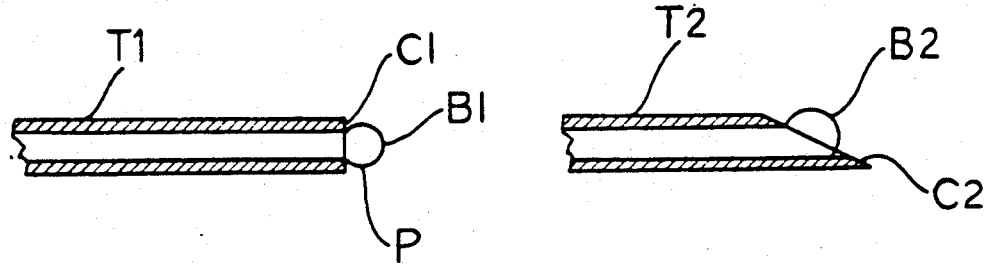
Fig. 3A
(PRIOR ART)
Fig. 3B

LEVEL MEASURING BUBBLER TUBE TIP

CROSS-REFERENCE TO RELATED APPLICATION

This application is a continuation-in-part of application Ser. No. 07/533,608 filed Jun. 5, 1990, now abandoned.

BACKGROUND OF THE INVENTION

1. Field of the Invention

This invention relates generally to liquid level measuring systems, and more particularly to an improved system employing bubbler tubes having improved tips to prevent variations in the bubble level.

2. Description of the Prior Art

In the prior art a purging bubbler tube system is employed for measuring liquid level. In such a system gas may be periodically allowed to flow through the bubbler tube to purge out any liquid that might have accumulated therein. At the end of the purge the gas is valved off. With the gas valve off the pressure in the bubbler tube will equalize at the head of liquid which is developed at the gas/liquid interface. The gas/liquid interface will be located within or immediately joining the bubbler tube. The pressure within the bubbler tube is measured by some type of instrumentation. The pressure measurement is made between purge periods. In such a purging bubbler tube system the depth of the gas/liquid interface is directly related to the pressure within the bubbler tube. Hence, for consistent pressure readings it is imperative that the gas/liquid interface depth be repeatable and constant for a given liquid level. In the prior art the tip of the bubbler tube in a purging bubbler tube system is generally the horizontal cut at the end of the vertical bubbler tube. The shortcoming of this design is that the gas/liquid interface depth for a given liquid level is not repeatable and constant. The non-repeatability of the gas/liquid interface depth is due to the periodic purge. When the purge valve is closed the depth of the gas/liquid interface is largely determined by the bubbles which the gas forms at the end of the bubbler tube. The gas/liquid interface may be outside of the bubbler tube, a bubble, and sometimes within the bubbler tube after the bubble has just broken off. Other times it will be between these two points. As mentioned previously the variation in gas/liquid interface depth causes a corresponding undesirable variation in the bubbler tube pressure.

Temperature and leaks are the major causes of the gas/liquid interface depth not being constant. Any temperature change of the gas in the bubbler tube after the purged gas is valved off will cause gas to expand or contract, causing the gas/liquid interface to either rise or fall. Any leak, either in the plumbing or the purge valve, will also cause the gas/liquid interface to either rise or fall. Again, this non-constant gas/liquid interface depth will cause unwanted variations in the bubbler tube pressure.

U.S. Pat. No. 4,630,478, Johnson, discloses a liquid volume sensor system employing two bubbler tubes which are bent at substantially a right angle at their ends in order to contain a cylinder 5 between the tips. Expansion of the cylinder 5 is used for temperature compensation by changing the spacing between the tips of the tubes. Johnson contains no disclosure about the desired length of the bend and does not show any slanted cutoff at the tips of the tubes. He does not address the problem of the present invention. There is no disclosure of the length of the bends being sufficient to solve the problem of the bubble backing up in the tube.

Of the patents cited in Johnson only U.S. Pat. No. 3,473,379 shows a right angle bend in the end of the pressure tube. However, the pressure sensors in this patent employ transducers in the tube and it is not a bubbler system.

Sci-Tec Instruments, Incorporated of Saskatoon, Canada makes a device called "Petro Tag," a hydrostatic system which uses a Teflon coated disk at the end of the bubbler tube to trap a big bubble to try to solve the same problem solved by the present invention.

Accordingly, it is an object of the present invention to provide a bubbler tube tip design to maintain the gas/liquid interface in a bubbler tube level measuring system at a constant depth.

Another object is to provide such a device in which any backing up of the bubble in the tube leaves the bubble at a constant depth.

Still another object is to provide a tip for the bubbler tube designed to prevent the bubble from sagging at the end of the tube, again to maintain a constant depth.

SUMMARY OF THE INVENTION

In the present invention a level measuring system is provided for measuring the level of a fluid in a tank which employs two or more tubes through which gas is passed, the tubes extending to different levels in the fluid, whereby the level may be measured by comparing the differences in pressure necessary to release bubbles from the tube, and employs an improvement comprising bending the end of each of the tubes at substantially a right angle for a length long enough to cause the bubbles to remain at a constant depth even though they back up in the tube, and cutting off the ends of the tube at an angle such that the gas/liquid interface of the bubbles are at a constant depth and are prevented from sagging at the end of the tube.

BRIEF DESCRIPTION OF THE DRAWINGS

FIG. 2 is a detailed cross-section of the inventive tip of a bubbler tube to be employed in the system of FIG. 1; and FIGS. 3a and 3b are useful in explaining the pressures within the bubbler tube and to illustrate the inventive advantage.

DESCRIPTION OF THE PREFERRED EMBODIMENT

Figure 1:
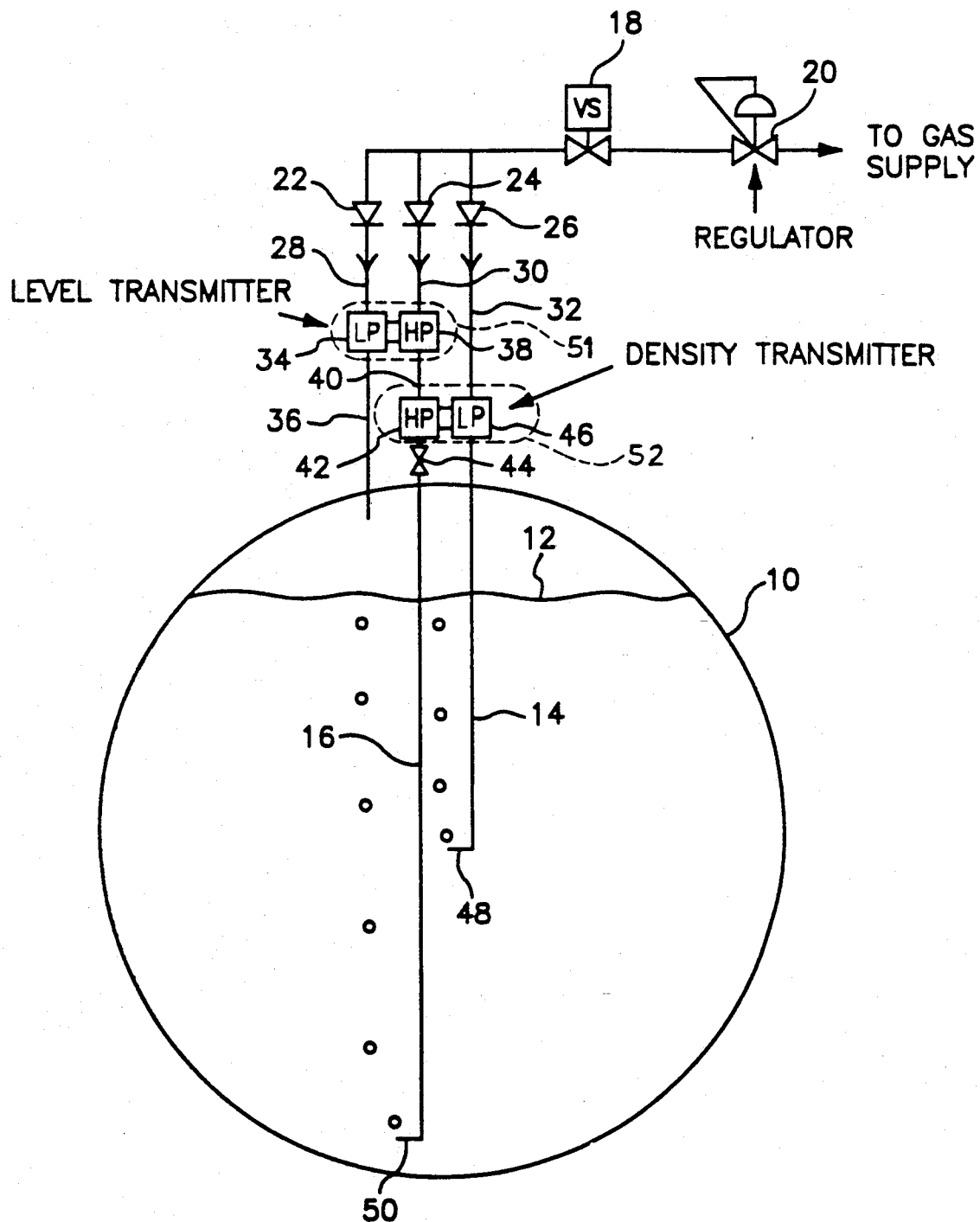
FIG. 1 is a cross-sectional sketch of a hydrostatic underground tank level system employing the invention.

Turning now to the drawings, in FIG. 1, a typical hydrostatic underground tank level system includes a tank 10 filled with fluid to a level 12 and employing two bubbler tubes 14 and 16 extending to different depths, in this example, 72 inches apart in depth. A two-way solenoid valve 18 is employed together with the regulator 20 which is connected to a source of nitrogen or instrument air supply together with check valves 22, 24 and 26 to feed air or nitrogen into the lines 28, 30 and 32, respectively. A level transmitter 51 has its low pressure (LP) side 34 connected in the line 28 and through a line 36 to the top of the tank 10 above the fluid level 12. The high pressure (HP) side 38 of the level transmitter 51 is connected from the line 30 through a line 40 to the high pressure (HP) side 42 of a density transmitter 52, which is connected in turn through an isolation valve 44 to the tube 16. The low pressure (LP) side 46 of the density transmitter 52 is connected from line 32 to line 14. Thus, when the solenoid valve 18 is opened the check valves will open and air or nitrogen will go down the three lines. The high pressure sides 38 and 42 of the level and density transmitter are connected in common to the bottom of the tank. The low pressure sides are connected above the fluid level and to the intermediate position below the fluid level. Thus, the density transmitter will provide the difference in pressure between the two bubbler tips immersed in the fluid and the level transmitter, the difference between the gas above the fluid level and the bottom of the tank, or the fluid level.

The equations for a typical system described above are:

(1) fluid level in the tank = inches of water column measured by the level transmitter / specific gravity of the fluid in the tank (2) specific gravity of the fluid in the tank = inches of water column measured by the density transmitter / 72

72 being the vertical distance between bubble tube tip 48 and bubbler tube tip 50 in inches equation (1) and (2) can be combined to give equation (3)

(3) fluid level in the tank = (inches of water column measured by the level transmitter / inches of water column measured by the density transmitter) ×72

(4) density of fluid in the tank = specific gravity of the fluid in the tank x water at base conditions The typical system described above is known from the prior art. The improvement of the present invention involves maintaining the gas/liquid interface between the bubbles at the ends of tubes 14 and 16 at a constant depth to avoid problems involved when the bubbles sag at the end of the tubes and when the bubble backs up the tube when the gas supply is shut off. In order to accomplish this, the ends of the tubes 14 and 16 contain substantially right angle bends 48 and 50, respectively. These bends are designed to be long enough so that any backing up of the bubbles in the tubes is horizontal rather than vertical, maintaining the bubbles at a constant depth. This feature is illustrated in more detail in FIG. 2 using the end of pipe 14, which is identical to the end of pipe 16. The right angle bend 48, as stated previously, is long enough so that any backing up of the bubbles will be horizontal rather than vertical. In addition, the tip of the bend 48 is cut off at an angle 49 so that the bubble will form at the end of the bend 48 and not droop over the tip end and go to a different depth causing a change in the gas/liquid interface. Temperature and leaks will not effect the gas/liquid interface depth as long as the interface is within the tubing running parallel to the surface of the liquid.

Referring additionally to FIGS. 3a and 3b, the following is an explanation of how the bubbler tube functions. Enough pressure must be applied to each of the bubbler tube lines 14 and 16 during the purge period to allow bubbles to escape from the end of the bubbler tubes 48, 50. For example, if the end of the bubbler tube was immersed in 100 inches of water, then more than 100 of inches of water column pressure would have to be applied during the purge to produce bubbles at the end of the bubbler tube. When the purge is stopped, the pressure in the bubbler tube will stabilize to the pressure that is exerted by the liquid at the depth of the gas/liquid interface. The reason for using a purging type bubbler system is that between purges the pressure in the bubbler tube line should be constant because the gas/liquid interface will be static. In reality the gas/liquid interface will not be completely static but will vary somewhat due to expansion and contraction of the gas in the bubbler tube due to temperature. Further the gas/liquid interface will move if there are any leaks in the check valves. By having the tip T1/T2 of the bubbler tube horizontal and long enough to maintain the gas/liquid interface within this horizontal section the movement of the gas/liquid interface will not affect the pressure within the bubbler tube because the gas/liquid interface will be maintained at a constant depth below the surface of the fluid. The angle cut C2 at the tip T2 of the bubbler tube is provided to keep the bubble B2 from sagging if due to temperature increases the gas within the bubbler tube expands forcing the gas/liquid interface outside of the enclosed horizontal section of tubing. It has been observed that when the gas/liquid interface escapes the confines of a horizontal section of tubing that is cutoff square C1, that the bubble B1 that forms at the end of the tube tip T1 will sag below the bottom inside wall of the tube. When this happens the pressure within the bubbler tube increases to the pressure at point P of the bubble B1. By providing an angled cut C2 at the end of the bubbler tube T2, the bubble B2 is allowed to escape without sagging and causing and increase in pressure within the bubbler tube.

The maintaining of a constant pressure within the bubbler tube by providing a horizontal bubbler tube tip which is long enough to keep the gas/liquid interface within the horizontal section and the angled cut at the end of the bubbler tube which allows the bubble to escape without an increase in pressure within the bubbler tube are the improvements made by this invention.

Since the principles of the invention have now been made clear, modifications which are particularly adapted for specific situations without departing from those principles will be apparent to those skilled in the art. The appended claims are intended to cover such modifications, as well as the subject matter described, and to only be limited by the true spirit of the invention.

I claim:

1. In a purging bubbler tube measuring system for determining the level of a fluid in a tank, employing at least two bubbler tubes through which gas is periodically passed, said tubes extending to different levels in or above said fluid, the improvement comprising bending the end of each of said tubes below the fluid level at substantially a right angle, forming a horizontal tube section in each of the tubes long enough such that the interface of the bubbles and the fluid are kept at a constant depth even though they should back up in the horizontal section of the tubes; and cutting off the tips of the bent tubes at an angle such that the bubbles will rest on the tip of the tubes and not sag over the end of the tube tips.

2. A bubbler tube used in a purging bubbler tube system in which a gas is periodically passed through the tube to measure a physical characteristic of a fluid by comparing the pressure required to release bubbles into the fluid with another reference pressure, comprising a vertical tube section immersed in the fluid, a substantially right angle bend at the end of said tube forming a horizontal section long enough such that the gas/liquid interface of the bubbles is kept at a constant depth even though the bubbles should back up in the horizontal section of the tube; and the tip of the horizontal section is cut off at an angle such that bubbles will rest on the tip and not sag over the end of the tube tip maintaining a constant pressure within the bubbler tube.

3. A method of maintaining a constant pressure within a bubbler tube used in a purging bubbler tube system in which gas is periodically passed through the tube to measure a physical characteristic of the fluid by comparing the pressure required to release bubbles into the fluid through the bubbler tube comprising the steps of providing, at the end of a vertical section of said bubbler tube, a horizontal bubbler tube tip section which is long enough to keep the gas/liquid interface within the horizontal section, and cutting the end of the horizontal section at an angle to allow the bubbles to escape without sagging and causing an increase in pressure within the bubbler tube.

* * * * *